United States Patent [19]

Baum et al.

[11] Patent Number: 4,841,223

[45] Date of Patent: Jun. 20, 1989

[54] METHOD AND APPARATUS FOR MEASURING FIBER ORIENTATION ANISOTROPY

[75] Inventors: Gary A. Baum; Charles C. Habeger, Jr., both of Appleton, Wis.

[73] Assignee: The Institute of Paper Chemistry, Appleton, Wis.

[21] Appl. No.: 63,580

[22] Filed: Jun. 17, 1987

[51] Int. Cl.⁴ .................. G01R 27/04; G01B 5/16
[52] U.S. Cl. .................... 324/58.5 A; 324/58.5 R; 73/159
[58] Field of Search ................ 73/159, 160; 162/198; 324/58.5 R, 58.5 A, 58.5 B, 58.5 C

[56] References Cited

U.S. PATENT DOCUMENTS

| 4,581,575 | 4/1986 | Osaki | 73/159 |
| 4,710,700 | 1/1987 | Osaki | 73/159 |

FOREIGN PATENT DOCUMENTS

| 244438 | 5/1969 | U.S.S.R. | 324/58.5 A |
| 245439 | 10/1969 | U.S.S.R. | 324/58.5 A |
| 318858 | 12/1971 | U.S.S.R. | 324/58.5 A |
| 441525 | 12/1974 | U.S.S.R. | 324/58.5 A |

Primary Examiner—Reinhard J. Eisenzopf
Assistant Examiner—Jose M. Solis
Attorney, Agent, or Firm—Fitch, Even, Tabin & Flannery

[57] ABSTRACT

Apparatus for measuring fiber orientation anisotropy in a web of fibrous material includes a microwave generator, a waveguide through which a microwave signal is propagated axially and in which an electric field is established in one direction perpendicular to the waveguide axis, the waveguide having a gripping means which provides a gripping means for specimen insertion, a detector for measuring intensity of the microwave signal propagated through the waveguide and a metering means for numerically evaluating the intensity of the propagated signal. The intensity of the propagated signal is measured (1) with the waveguide empty, (2) with the specimen inserted in the waveguide in a plane normal to the axis and with its machine direction aligned with the electric field and (3) with the specimen inserted in the waveguide in the normal plane and with its cross direction aligned with the direction of the electric field. The ratio of attenuations by the specimen in the two orientations is a measurement of fiber orientation anisotropy.

16 Claims, 1 Drawing Sheet

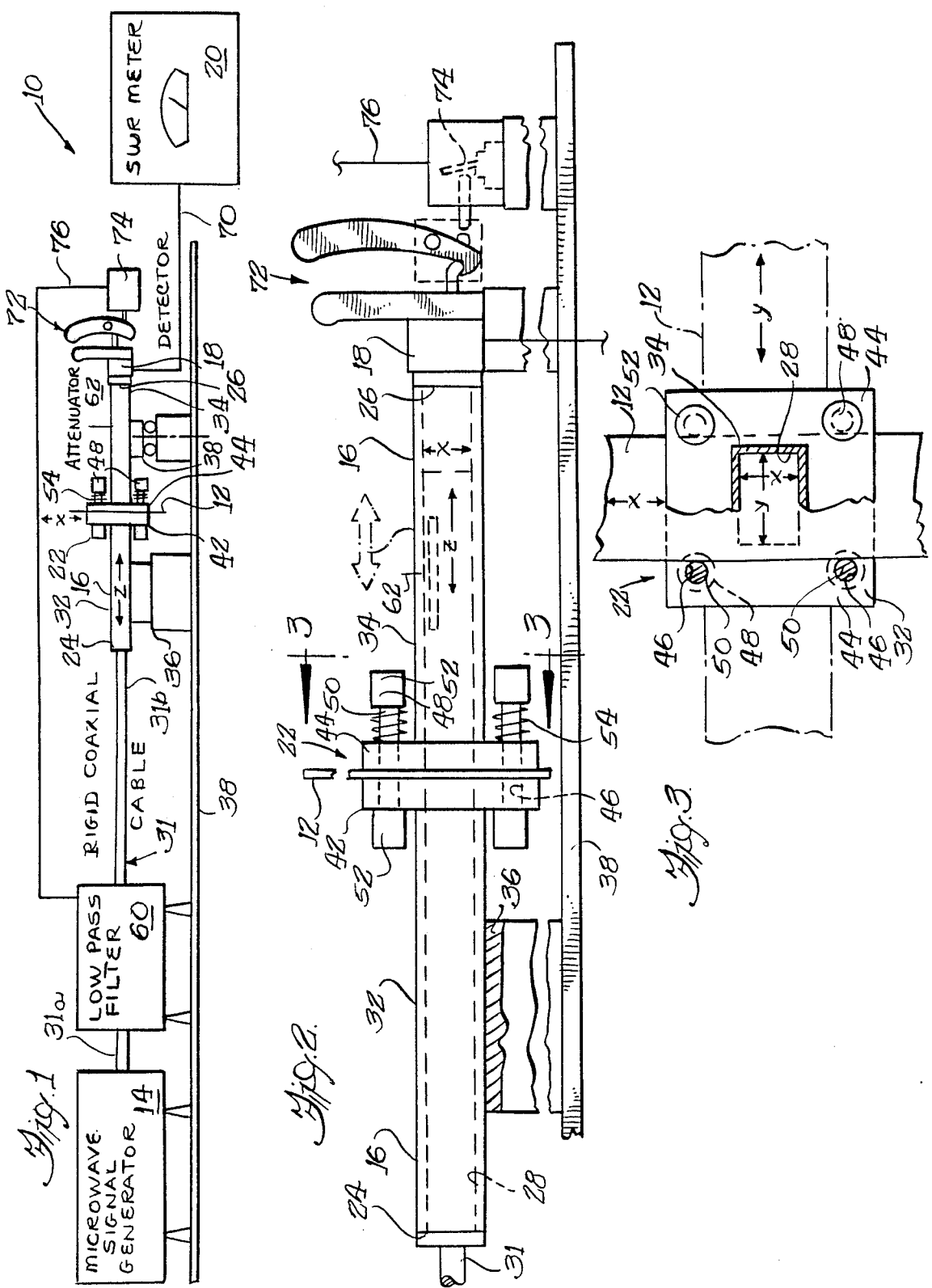

METHOD AND APPARATUS FOR MEASURING FIBER ORIENTATION ANISOTROPY

The present invention is directed to methods and apparatus for measuring fiber orientation anisotropy in fibrous materials.

BACKGROUND OF THE INVENTION

Fiber-containing materials, such as paper, paperboard or the like, are usually formed in continuous processes, producing continuous webs in the form of sheets or rolls. Although such webs are formed from a slurry of randomly oriented fibers, the machines used for formation of the webs tend to align the fibers in the machine direction (MD), that is, in the direction in which the webs are formed. The alignment of fibers in the machine direction imparts different properties to the web in the MD than in the perpendicular or cross-machine direction (CD). For example, the web may tear more easily, but more evenly, in the MD than in the CD.

For many applications, it is desirable to keep random fiber orientation anisotropy (FOA) to a minimum, and there is a need to monitor samples of the web to measure the degree of fiber orientation anisotropy. Some applications, on the other hand, may make advantageous use of a certain degree of anisotropy, and in such cases also, it is necessary to monitor samples of the web to ensure that the degree of fiber orientation anisotropy falls within a specified range. Further, orientation ratios across the web can be important to provide product uniformity.

Presently, fiber orientation anisotropy measurements are conducted by direct observation, x-ray diffraction, and laser transmittance techniques. The first determinations or fiber orientation distributions were made on sheets with a small added portion of dyed fibers. The angles of orientation of thousands of dyed fiber segments were manually measured. This provides a direct measure of the orientation, but it is tedious, requires specially prepared sheets, and only measures surface properties. Anisotropy in x-ray diffraction patterns is also used as a laboratory indicator of FOA. Recently, the diffraction pattern of transmitted laser light has been used to infer FOA on very thin sheets. On sheets of moderate thickness, FOA is estimated from the pattern of forward scattered light. Laboratory and on-line instruments based on the scattering principle have been commercially available. The microwave technology, described here, is complementary to the other techniques. A major advantage is that microwaves penetrate very heavy sheets. Also, microwaves have been heretofore used extensively to measure paper moisture content on-line, and a moderate modification of this established technique could lead to fiber orientation as well as moisture content information. However, there exists a need for rapid, simple tests for detecting FOA that are nevertheless reliable and repeatable, and it is a primary object of the invention to provide methods and apparatus for measuring FOA.

SUMMARY OF THE INVENTION

The present invention provides apparatus for performing a method of measuring FOA in a specimen of fibrous material based upon differential attenuation of microwaves by the specimen placed in different orientations relative to the orientation of an electric field. The apparatus provides a means for generating microwaves and a waveguide in which the microwaves are channelled in an axial or z direction, and in which the electric field is aligned along a first or x direction of an x,y plane that is normal to the z direction. The fibrous material specimen is placed in the path of the microwaves in the x,y plane, at one time with its MD oriented in the x direction and at another time with its MD oriented in the y direction. The attenuation by the web of the microwaves with its MD aligned in each of the x and y directions, compared to the non-attenuated signal, is detected and measured, and a ratio of attenuation in the x and y directions is calculated, the ratio of attenuation, indicating the degree of FOA.

BRIEF DESCRIPTION OF THE DRAWINGS

FIG. 1 is a diagrammatic view of apparatus embodying various features of the invention;

FIG. 2 is an elevation view, partially cut away, of the waveguide, waveguide attenuator, detector and switch of the apparatus shown in FIG. 1 and the mounting means therefor; and FIG. 3 is a cross-sectional view taken along line 3—3 of FIG. 2.

DETAILED DESCRIPTION OF THE PREFERRED EMBODIMENTS

In accordance with the present invention, apparatus, indicated generally at 10, is provided for performing a process of measuring FOA of a specimen 12 of fibrous material by the amounts of attenuation of a microwave signal directed in an axial z direction through a microwave waveguide 16 by the specimen (a) with its MD oriented in the x direction (FIG. 3) of the electrical field and (b) with its MD oriented in the y direction perpendicular to the electric field. The attenuation of microwaves by a fibrous material specimen disposed in the x,y plane normal to the z direction of the microwaves depends on the real and imaginary parts of the dielectric constant in the specimen 12, and on specimen thickness. Due to preferred fiber orientation along the MD, the effective dielectric constant of the specimen 12 is greater when the MD is aligned in the x direction of the electric field than when the CD is aligned in the x direction. With the specimen 12 oriented with its MD in the direction of the electrical field, i.e., the x direction, the attenuation of the microwave signal is greater than when the specimen is oriented with its MD perpendicular to the electrical field, i.e., in the y direction. The ratio of attenuation with the MD in the x direction compared to the ratio of attenuation with the MD in the y direction is a measure of FOA.

Apparatus for measuring microwave attenuation includes a microwave signal generator means 14, a waveguide means 16 through which microwaves are guided in the axial or z direction with an electric field aligned in the x direction, means 22 for orienting the fibrous material specimen 12 in the x,y plane perpendicular to the z direction within the waveguide 16 so that the MD of the specimen may be alternately oriented in each of the x and y directions, means 18 for detecting the specimen-attenuated microwave signal and metering means 20 for evaluating the level of the detected signal.

Briefly, the specimen 12, which comprises either a web of fibrous material or layers of web with each layer having its, MD, aligned in the same direction, is held within a gripping means 22 in the waveguide 16 with its MD aligned in the x direction; a microwave signal is propagated through the waveguide from an input end 24; the attenuated microwave signal is received by the detector 18 at an output end 26 of the waveguide 16; and its intensity is evaluated, e.g. as a numerical value by the meter 20. Then the specimen is reoriented in the x,y plane with the CD aligned in the x direction (the MD in the y direction) and the process of microwave attenuation measurement is repeated. The degrees of attenuation by the specimen in the two orientations, which is the level of the detected signal subtracted from the level of the signal detected without the specimen ("no specimen" value) in the waveguide 16, are compared. For example, a ratio is obtained by dividing the attenuation by the specimen with its MD oriented in the x direction by the attenuation by the specimen with its MD oriented in the y direction.

The waveguide 16 is a standard X-band rectangular wave guide that has a channel 28 that is rectangular in cross section. Preferably, one direction of the waveguide channel, e.g., the vertical direction, is substantially shorter than the horizontal direction. In a waveguide in which the channel in one direction is shorter than in the other, the electrical field is preferably set up along the shorter dimension, which becomes the x direction for purposes of disclosure herein, and the wider dimension becomes the y direction. A typical waveguide 16 for use in accordance with the invention has an x dimension of between 0.5 and 2 cm. whereas the y dimension is between about 1 cm and about 6 cm. The choice of appropriate waveguide channel dimensions depends on the frequency of the microwave signal. The axial length of the waveguide 16 between the input end and the output end is typically between about 30 and about 50 cm. long with the gripping means 22 for specimen insertion disposed approximately midway between the ends. The input end of the waveguide 16 is connected to the microwave signal generator by means of a coaxial cable 31a, 31b.

In order that microwave attenuation by a specimen 12 may be measured with the specimen inserted with its MD alternately aligned in each of the x and y orientations and also so that a measurement of signal level may be made without the sample inserted, the openable and closable gripping means 22 is provided for insertion of the specimen aligned in the x,y plane in alternate orientations. The gripping means 22 fully closes on the specimen 12 to grip the same and ensure that microwave signal is not lost.

As a preferred gripping means 22, the waveguide 16 according to the invention, includes a rearwardly extending guide tube 32 which is connected to the coaxial cable 31a, 31b that transmits a microwave signal from the signal generator 14 and a forwardly extending guide tube 34 that terminates in its connection to the detector 18. The guide tubes 32, 34 are axially reciprocal relative to each other to alternately open and close the gripping means 22 therebetween. In the illustrated embodiment, the tube 32 is supported by a rigid mount 36 on a platform 38, whereas the tube 34 and detector 18 are slidably mounted on a block 40 on the platform 38 [for reciprocal movement in the axial or z direction]. Each of the tubes 32, 34 has an outwardly extending rectangular flange 42, 44 at the junction of the two tubes for holding the specimen 12 therebetween across the entire cross section of the waveguide channel 28. As a means for maintaining axial alignment of the tubes 32, 34, four holes 46 extend through the opposed flanges 42, 44 and four guide bolts 48 extend through the aligned holes. The threaded portion 50 of the bolts 48 engage end heads and/or nuts 52 and are sufficiently long to permit reciprocal movement of the tube 34. Springs 54 are mounted on each of the guide bolts 48 between of the heads 52 and the flange 44 of the tube 34, the springs acting on the flange 44 to bias the tube 34 toward the tube 32 so as to close the gripping means. Thus, the gripping means 22 can be manually opened to receive or rotate the specimen 12.

Although the channel 28 through the waveguide 16 has a greater dimension in the y direction than in the x direction, the flanges 42, 44 extend sufficiently to allow the guide bolts 48 to be arranged in a square configuration, whereby a first specimen-receiving pathway is defined between the bolts in the x direction and a second specimen-receiving pathway of equal width is defined between the bolts in the y direction. Thus, when a specimen 12 is cut it is matched to the specimen-receiving pathway between the bolts in either the x or y direction. Insertion into the gripping means 22 allows the MD to be in substantial alignment with either the x or the y direction.

The microwave signal generator 14 may be selected from commercially available generators. The microwave frequency for purposes of this invention is between about 2 and about 20 GHz, and preferably between about 7 and about 12.5 GHz. For purposes of this invention, the microwave signal generator is pulsed at a much lower frequency, e.g., between about 0.1 and about 10 kHz. The amplitude of the microwave signal is preferably between about 10 and about 40 decibels.

Preferably, and as illustrated, the apparatus 10 includes a low pass filter 60 for eliminating spurious low frequency signals. The microwave signal generator 14 is connected to the low pass filter 60 by a rigid coaxial cable segment 31a, and the low pass filter 60 is likewise connected to the waveguide by a coaxial cable segment 31b.

Associated with the reciprocable tube 34 of the waveguide 16 is a waveguide attenuator 62 which is found to be important in providing reproducible readings. Early tests conducted without an attenuator gave unsatisfactory results because of the large standing wave ratio in the waveguide 16. The loss was not linear with the number of web layers inserted, and sometimes there were unreasonably high or low readings. The attenuator 62 helps to provide reproducible readings by preferentially reducing multiply reflected components in the signal. The attenuation setting of the attenuator should be between about 10 and 20 dB times the intensity of the generated microwave signal.

The detector 18, which is mounted at the output end 26 of the tube 34, includes means for receiving the microwave signal and rectifying the detected microwave signal to produce an electrical wave signal having the frequency of the pulse and an intensity proportional to the received microwave signal, either with the waveguide channel void or with the specimen 12 inserted across the microwave channel 28. In a preferred embodiment, the detector 18 contains a low barrier diode which rectifies the received microwave signal. [to a square wave signal of the frequency of the pulse].

The meter 20 is connected by an electrical conduit 70 to the detector 18 and evaluates the level of the signal received by the detector 18, assigning the signal a numerical value, e.g., a decibel reading. For use with a detector 18 which generates a rectified wave signal, the meter 20 is a standing wave ratio meter which has a narrow band amplifier centered at the pulse frequency rate and registers in decibels the incoming signal, e.g., on a needle dial.

A hand lever 72 is associated with the detector end of the waveguide 16 for reciprocating the tube 34 rearward and forward to alternately open and close the gripping means 22. With the gripping means open, the specimen 12 is inserted, then, the gripping means is closed upon the inserted specimen. Associated with the hand lever 72 is an on-off switch 74 which is connected by an electrical conduit 76 to the microwave signal generator 14 for actuating the microwave signal generator when the tube 34 is moved forward to close the gripping means, and inactivating the microwave signal generator when the rearward tube is moved rearward to open the gripping means. When the gripping means 22 is closed, the microwave signal generator 14 should emit a continuous, pulsed microwave signal which is received by the detector 18 and results in a meter reading in decibels. Because the signal generator 14 is off during insertion, some time is required to achieve a steady state and, as a result, the actuation process, following specimen insertion, certain artifactual signals are introduced. The microwave signal is propagated through the specimen for a sufficient time for the meter 20 to stabilize before a reading is taken.

It is found that the above-described apparatus 10 is very sensitive to small movements of the signal generator 14 and the waveguide 16, to small movements of connecting coaxial cable 31 and to variability of the seating of the specimen 12 within the waveguide. For this reason, the signal generator 14, filter 60, waveguide 16, attenuator 62 and detector 18 are preferably mounted to the common rigid base or platform 38. Also, rigid, rather than flexible, coaxial cables 31a and 31b are used to connect the generator 14, filter 60 and waveguide 16.

The measuring procedure according to the invention is preferably conducted on various portions of specimens 12 in order to obtain a reading that averages several measured values. This averages out sheet variability and increases the signal-to-noise ratio in the attenuation reading. As a means to simply provide several readings, specimens are provided in strip form, cut longitudinally both in the MD and CD directions, the width of the strips being matched to the insertion pathways between the guide bolts 48 of the gripping means 22 and the length being considerably longer. Each specimen 12 is marked at intervals along its length for alignment with an edge of the flanges 42, 44, and these marks are successively aligned at the flange edge to place different portions of the strip across the waveguide channel 28 and thereby provide for multiple readings. Typically, four marks will be made on each specimen, the marks being spaced apart sufficiently so that a completely new portion of each specimen is measured for attenuation upon alignment of each mark. The readings at each alignment position of a strip specimen moved through the gripping means in any one direction are used to provide an average attenuation ratio.

The process as described above could conceivably be performed using a single strip specimen 12 passed through the gripping means 22, first in the vertical direction and then in the horizontal direction, providing both an MD direction reading and then a CD direction reading. However, it is found that boundary conditions at the gripping means interface are different for the horizontal and vertical insertion directions. Thus, in the most simple practice of the method according to the invention, readings with the MD aligned in each of the x and y direction of the waveguide would provide a ratio of attenuation readings which might be meaningful for a particular type of fibrous web, either by establishing normal ratio values for that type of material or by correlating the ratio with anisotropy measurements obtained by other methods. However, the ratio thus obtained would generally not be obviously reflective of fiber orientation anisotropy. That is, ratios derived from single specimens vary according to their anisotropy, but the ratios obtained are not in themselves reflective of the degrees of anisotropy without reference to a predetermined table or the like. For example, whereas a perfectly isotropic specimen will attenuate a microwave signal equally on any direction and therefore should provide a ratio of attenuation when its MD is aligned in the x direction to attenuation when its MD is aligned in the y direction of unity, when the attenuation ratio of the perfectly isotropic single specimen is determined in apparatus with asymetric boundary conditions, the ratio may be quite different than unity.

To overcome the problem of misleading ratios caused by the asymetrical nature of the apparatus and specimens, a strip specimen that is cut lengthwise in the machine direction and a strip specimen that is cut lengthwise in the cross direction are preferably used for providing a composite measurement of attenuation ratio that is reflective of FOA. Each of the MD-cut and CD-cut strip specimens is passed through the gripping means 22 in each of the vertical or x direction and the horizontal or y direction. Accordingly, each specimen 12 is used to provide an MD attenuation reading and a CD attenuation reading. To obtain a ratio using an MD-cut strip and a CD-cut strip the MD (x alignment) direction attenuation of the MD-cut specimen is added to the MD (y alignment) direction attenuation of the CD-cut specimen to obtain a summed attenuation of the MD aligned in the x direction. Likewise, the CD (y alignment) direction attenuation of the MD-cut specimen is added to the CD (x alignment) direction attenuation of the CD-cut specimen to obtain a summed attenuation of the CD aligned in the x direction. Then the summed attenuation of the MD aligned in the x direction is divided by the summed attenuation of the CD aligned in the x direction, giving an MD/CD ratio ($R_M$) that eliminates boundary condition artifacts. By using specimens cut in both directions to provide an attenuation ratio of $R_M$, the ratio is reflective, on its face, of anisotropy. Within experimental limits, a perfectly isotropic specimen, should be unity, and greater anisotropy should provide $R_M$'s greater than unity, reflective of greater microwave signal attenuation in the machine direction.

When each strip is read at four different locations in each direction, sixteen different readings are taken, and four different $R_M$'s may be calculated and then averaged. The first MD (x direction) value for the MD-cut strip is added to the first MD (y direction) value for the CD-cut strip; the first CD (y direction) value for the MD-cut strip is added to the first CD (x direction) value for the CD-cut strip; and the summed MD values are divided by the summed CD values to obtain a first attenuation ratio $R_{M(1)}$. Second, third and forth ratios, $R_{M(2)}$, $R_{M(3)}$ and $R_{M(4)}$ are obtained and averaged to obtain an $R_M$.

As noted above, the specimen or strip may be either a single sheet of fibrous material or may be a stack of sheets. A single sheet may be sufficient to provide a sufficiently high signal to noise ratio when the material is relatively thick, e.g., thick paperboard. However, when thin sheets, such as sheets of paper, are measured for FOA, it is desirable to overlay a plurality of such sheets. With the apparatus currently in use, it is found that a total thickness of about 1 mm, and preferably at least about 1.5 mm, is desired to achieve a good signal-to-noise ratio. A specimen comprising a plurality of overlaid sheets may be made up by cutting a plurality of strips of similar length and width longitudinally in the same orientation (MD or CD) and joining them together at one end, e.g., with a staple. The stack of strips is multiply marked for alignment with the flange edge and then inserted through the gripping means, joined end first, to the first mark, an attenuation reading taken and the process repeated at each mark and then in a similar manner at each mark in the opposite direction.

The invention will now be described in greater detail by way of specific examples

EXAMPLE 1

The microwave signal generator 14 is a Polarad model 1108A-C X-band with a frequency range of 6.95 to 12.4 Ghz. An amplitude modulation microwave signal of 20 decibels is pulsed on and off with a 50% duty cycle at a 1 kHz rate. The amplitude modulated microwave signal is filtered through a Hewlett Packard 11686A low pass filter 60 to eliminate spurious low frequency signals. The signal is carried through a rigid coaxial cable 31b to a rectangular waveguide 16 which has a channel 2.286 cm. wide and 1.016 cm. high. The coaxial cable 31b is connected to the waveguide 16 so that the electric field is oriented vertically along the smaller (x) dimension. The waveguide 16, including its tubes 34, 32, is 42 cm. long, the tube 32 being 19 cm. long with the coaxial cable 31b attached at its front end. Tube 34 includes a Systron Donner DBG 430 variable, microwave attenuator 62. The attenuator 62 is set at 10 dB. Mounted at the end of the tube 34 is a Systron Donner DBG 310 detector means 18 which contains an Alpha Industries DDC4561D low barrier Schottky diode which rectifies the specimen-attenuated signal to produce a 1 kHz square wave. The square wave signal is transmitted to a Hewlett Packard 415E standing wave meter 20 which is a narrow band amplifier centered at 1 kHz that registers in decibels the incoming signal on a needle dial.

A sheet of 42 pound liner board is cut into strips 2.78 cm. wide and 15 cm. long, longitudinal strips oriented in both the MD and CD being cut. Four strips cut longitudinally in each direction are stacked to a thickness of 1.5 mm. and stapled at one end to provide two specimens 12. Four small edge marks 2.5 cm. apart are made on each stack toward the linear center of the stack.

With the gripping means 22 closed and no specimen in the waveguide 16, a "no specimen" meter reading is taken. The lever 72 is pulled to open the gripping means and the MD-cut stack is inserted vertically until one of the edge marks is flush with an edge of the flanges. The gripping means 22 is closed, whereupon the switch is actuated to activate the signal generator 14. Thirty seconds are allowed for the meter 20 to stabilize. The meter reading is recorded and subtracted from the "no specimen" value. The process is repeated at each of the marks. Next, the MD-cut strip is inserted horizontally, and readings taken at each of the marks. The CD-cut stack is handled in a similar manner. The values of the sixteen readings (subtracted from the "no specimen" value) and calculated $R_M$'s are given in the table below.

|   | MD-cut vertical dB | CD-cut horizontal dB | MD-cut horizontal dB | CD-cut vertical dB | $R_M$ |
| --- | --- | --- | --- | --- | --- |
| A | 1.181 | 1.303 | 1.098 | 1.213 | 1.075 |
| B | 1.188 | 1.315 | 1.103 | 1.218 | 1.078 |
| C | 1.178 | 1.285 | 1.055 | 1.218 | 1.084 |
| D | 1.183 | 1.320 | 1.110 | 1.208 | 1.080 |

Average $R_M = 1.079$.

EXAMPLE 2

Using the apparatus described in Example 1 a specimen 12 of paperboard 092 mm. thick is examined in the manner described above. Because of the thickness of the paperboard, there is no need to stack the strip, and it is sufficient to measure FOA on one thickness. The results are given in the table below.

|   | MD-cut vertical dB | CD-cut horizontal dB | MD-cut horizontal dB | CD-cut vertical dB | $R_M$ |
| --- | --- | --- | --- | --- | --- |
| A | 1.71 | 2.70 | 2.53 | 1.53 | 1.089 |
| B | 1.78 | 2.72 | 2.555 | 1.505 | 1.108 |
| C | 1.76 | 2.765 | 2.56 | 1.560 | 1.098 |
| D | 1.73 | 2.725 | 2.555 | 1.535 | 1.089 |

Average $R_M = 1.096$.

The value $R_M$ obtained by this test is a ratio of signal attenuation by a specimen oriented in two perpendicular directions relative to the electrical field direction. This ratio may be used in itself as a quality control once a permissible $R_M$ range has been established for a particular type of fibrous material. For any particular type of fibrous material, $R_M$ values may be correlated with FOA parameters established in other types of tests.

While the invention has been described in terms of certain preferred embodiments, modifications obvious to one with ordinary skill in the art may be made without departing from the scope of the present invention. For example, while the measurement process according to the invention has been described in terms of recording meter readings and tabulating attenuation values, it is contemplated that more sophisticated apparatus will include computing means linked to the meter, whereby readings may be tabulated and individual and average $R_M$ values calculated automatically.

Various features of the invention are set forth in the following claims:

What is claimed is:

1. Apparatus for measuring fiber orientation anisotropy in a web of fibrous material that has a machine direction and a cross direction, the apparatus comprising:
   a waveguide having a first end and a second end and gripping means between said ends for insertion of a specimen of the web in a plane normal to the waveguide axis and alternately with its machine direction aligned in each of two orientations,
   a microwave signal generator for generating a test signal at a single, constant frequency,
   conduit means for conducting a generated microwave test signal from signal generator to said first end of said waveguide so as to propagate the microwave test signal from said first end to said second end with an electric field established in one of the perpendicular directions, detector means at said second end having a narrow band sensitivity for receiving a preferentially filtered constant frequency test signal propagated (1) through said waveguide with the waveguide empty of said specimen, (2) with the microwave signal attentuated by said specimen oriented in the first of said orientations and (3) with the specimen oriented in the second of said orientations, said detector means rectifying said received microwave signal to produce an electrical signal proportional to the intensity of the microwave signal received thereby.

waveguide attenuator means disposed in said waveguide between said gripping means and said detector for preferentially filtering reflected waves from the propagated microwave test signal, and metering means for receiving the electrical signal from said detector means and evaluating the intensity thereof.

2. Apparatus according to claim 1 including filter means for filtering low frequency signals from the signal generated by said microwave signal generator prior to transmission of said signal to said waveguide.

3. A process for measuring the fiber orientation anisotropy in a web of fibrous material that has a machine direction and a cross direction, the method comprising generating a microwave test signal at a single, constant frequency, propagating said microwave test signal through a waveguide along an axial direction from a first end to a second end and establishing an electric field in said waveguide in a first linear direction within a plane perpendicular to said axial direction, disposing a test specimen in the waveguide between the ends thereof so as to attenuate the test signal, preferentially attenuating reflected waves from the propogated test signal using a waveguide attenuator means disposed between the test specimen and the second waveguide end, detecting the intensity of the microwave signal at said second end with no specimen therein, disposing a specimen of said fibrous material in said waveguide in a plane normal to said axial direction, (1) at one time with the machine direction of the specimen aligned in the electric field direction and (2) at another time with the machine direction aligned at an angle to the electric field direction, detecting the intensities of the constant frequency microwave test signal at said second end with the specimen inserted aligned in each direction and, in each case, calculating the attenuation of the signal relative to the signal intensity with no specimen, and evaluating fiber orientation anisotropy according to the differential attenuation of the specimen aligned in the two alternate directions.

4. Apparatus according to claim 1 including a unitary platform on which said signal generator and said waveguide are mounted.

5. Apparatus according to claim 1 wherein said conduit means is rigid coaxial cable.

6. Apparatus according to claim 1 wherein said waveguide includes a rearward tube and a forward tube, said tubes being axially reciprocable relative to each other to provide a closable gripping means therebetween.

7. Apparatus according to claim 6 including a platform, means for rigidly mounting one of said tubes to said platform and carriage means for reciprocably mounting the other of said tubes.

8. Apparatus according to claim 1 wherein said waveguide has a rectangular channel having one dimension between about 1.5 and about 3 times larger than the other dimension.

9. Apparatus according to claim 8 wherein said electric field is established along the shorter dimension.

10. Apparatus according to claim 1 wherein said microwave frequency is between about 7 and about 20 GHz.

11. Apparatus according to claim 1 wherein said microwave signal is pulsed at a frequency of between about 0.1 and about 10 kHz.

12. Apparatus according to claim 11 wherein said detector means produces an electrical wave signal at the pulse frequency of said generator.

13. Apparatus according to claim 1 including switch means operably associated with said gripping means for actuating said generator when the said gripping means is closed and deactivating said generator when the said gripping means is opened.

14. A method according to claim 3 wherein said specimen comprises a plurality of layers of said fibrous material, each layer having its machine direction aligned in the same direction.

15. A method according to claim 3 wherein a first specimen is elongated in the machine direction, a second specimen is elongated in the cross direction, attenuation by each of the specimens is determined in each of the two perpendicular directions and a ratio is determined by dividing (A) the summation of the attenuations of the machine direction-elongated specimen with its machine direction aligned with he electrical field and the cross direction-elongated specimen with its machine direction aligned with the electrical field by (B) the summation of the attenuation of the machine direction-elongated specimen with its cross direction aligned with the electrical field and the cross directional-elongated specimen with its cross direction aligned with the electrical field.

16. A method according to claim 15 wherein attenuation measurements are taken at a plurality of locations along each elongated specimen, and fiber orientation anisotropy is evaluated reflecting the attenuations at the various locations along the specimens.

* * * * *